United States Patent [19]

Breitbart et al.

[11] Patent Number: 5,700,289

[45] Date of Patent: Dec. 23, 1997

[54] TISSUE-ENGINEERED BONE REPAIR USING CULTURED PERIOSTEAL CELLS

[75] Inventors: Arnold S. Breitbart, Great Neck; Daniel A. Grande, Sea Cliff, both of N.Y.

[73] Assignee: North Shore University Hospital Research Corporation, Manhasset, N.Y.

[21] Appl. No.: 545,988

[22] Filed: Oct. 20, 1995

[51] Int. Cl.$^6$ .................................. A61F 2/28; A61F 2/54
[52] U.S. Cl. .................................. 623/16; 623/66
[58] Field of Search .................... 623/11, 16, 66; 424/422, 423, 424, 425, 426, 577; 530/838, 840

[56] References Cited

U.S. PATENT DOCUMENTS

| | | | |
|---|---|---|---|
| 5,069,905 | 12/1991 | Lidor et al. | 424/423 |
| 5,171,310 | 12/1992 | Chisena | 602/5 |
| 5,197,985 | 3/1993 | Caplan et al. | 623/16 |
| 5,226,914 | 7/1993 | Caplan et al. | 623/16 |
| 5,324,294 | 6/1994 | Elia | 606/76 |
| 5,439,951 | 8/1995 | Glimcher et al. | 424/423 |
| 5,486,359 | 1/1996 | Caplan et al. | 424/93.7 |
| 5,518,680 | 5/1996 | Cima et al. | 264/401 |
| 5,533,836 | 7/1996 | Moore | 435/240.31 |
| 5,565,502 | 10/1996 | Glimcher et al. | 623/16 |

*Primary Examiner*—Debra S. Brittingham
*Attorney, Agent, or Firm*—Arnall Golden & Gregory, LLP

[57] ABSTRACT

Periosteal cells have been grown in cell culture and have been shown to have an osteoblastic phenotype, with production of osteocalcin and glycosaminoglycan. When seeded into polymeric implants, repair of critical size cranial defects was demonstrated and was confirmed by histology, biochemical assays, and radiodensitometry.

15 Claims, 3 Drawing Sheets

TISSUE-ENGINEERED BONE REPAIR USING CULTURED PERIOSTEAL CELLS

BACKGROUND OF THE INVENTION

The present invention is generally in the area of methods for repair and reconstruction of bone.

Bone is built of a dense network of collagen protein fibers arranged in layers with crystals of calcium phosphate and calcium carbonate between the fibers. About 25% of the bone's weight is calcium. About four percent of the bone's volume, scattered evenly throughout it, are living cells called osteocytes. These are supplied with oxygen and nutrients through a network of very small blood vessels that extend throughout the bone. Defects in the bone are repaired by osteoclasts removing the damaged bone, then osteoblast cells laying down new bone. The osteoblasts repeatedly form layers, each consisting of a network of collagen fibers, which produce enzymes resulting in calcium and phosphorus deposition, until the defect is repaired.

Bone repair has been primarily achieved using bone cements, pins, screws and other devices for mechanical stabilization. Larger defects, however, arising from trauma or surgery, require replacement of the missing bone with a material that provides support and which can be immobilized, yet which is also biocompatible. A graft may be necessary when bone fails and does not repair itself in the normal amount of time or when bone loss occurs through fracture or tumor. Bone grafts must serve a dual function: to provide mechanical stability and to be a source of osteogenesis. Since skeletal injuries are repaired by the regeneration of bone rather than by the formation of scar tissue, grafting is a viable means of promoting healing of osseous defects, as reviewed by Friedlaender, G. E., "Current Concepts Review: Bone Grafts," *Journal of Bone and Joint Surgery*, 69A(5), 786–790 (1987). Osteoinduction and osteoconduction are two mechanisms by which a graft may stimulate the growth of new bone. In the former case, inductive signals of little-understood nature lead to the phenotypic conversion of connective tissue cells to bone cells. In the latter, the implant provides a scaffold for bony ingrowth. The bone remodeling cycle is a continuous event involving the resorption of pre-existing bone by osteoclasts and the formation of new bone by the work of osteoblasts. Normally, these two phases are synchronous and bone mass remains constant. However, the processes become uncoupled when bone defects heal and grafts are incorporated. Osteoclasts resorb the graft, a process which may take months. More porous grafts revascularize more quickly and graft resorption is more complete. After the graft has been resorbed, bone formation begins. Bone mass and mechanical strength return to near normal.

Present methods for the repair of bony defects include grafts of organic and synthetic construction. Three types of organic grafts are commonly used: autografts, allografts, and xenografts. An autograft is tissue transplanted from one site to another in the patient. The benefits of using the patient's tissue are that the graft will not evoke a strong immune response and that the material may or may not be vascularized, which allows for speedy incorporation. However, using an autograft requires a second surgery, which increases the risk of infection and introduces additional weakness at the harvest site. Further, bone available for grafting may be removed from a limited number of sites, for example, the fibula, ribs and iliac crest. An allograft is tissue taken from a different organism of the same species, and a xenograft from an organism of a different species. The latter types of tissue are readily available in larger quantities than autografts, but genetic differences between the donor and recipient may lead to rejection of the graft. Periosteal and perichonchondral grafting has also been attempted, as described by Ritsila, et al., *Clin. Orthop. Related Res.* 302, 259–265 (1994). Examples of synthetic materials which have been used include titanium and steel alloys, particularly those having a porous structure to allow ingrowth of cells to stabilize the implant, bone cements, alone or mixed with cells, sterilized bone, and polymeric or polymeric/hydroxyapatite implants. Bioerodible polymers have been used in people for thousands of years, with plain gut (collagen) sutures being used since 175 A.D.(12), as reported by Chu, In *Biocompatible Polymers, Metals and Composites*, ed. Szycher, M, p. 477 (Technomic Publishing Lakewood, N.J. 1983). The first synthetic biodegradable biopolymers, polylactic acid and polyglycolic acid, were suggested for in vivo use in U.S. Pat. No. 3,371,069 to Schmidt. All have advantages and disadvantages, yet none provides a perfect replacement for the missing bone.

Large defects are particularly difficult. One approach has been to seed fibrous biodegradable polymeric matrices with bone-forming cells, then overlay the matrix onto the defect. As the cells proliferate, and surrounding tissues grow into the defect, the matrix will degrade, leaving the new tissue. As described in U.S. Pat. No. 4,846,835 to Grande and U.S. Pat. No. 5,041,138 to Vacanti, et al., cartilage has been grown by seeding synthetic polymeric matrices with dissociated cells, which are then implanted to form new cartilage.

The first description of bone cells in culture was by Peck, et al., in *Science* 146, 1476 (1964). Since that time, many studies have focused on the maintenance of viable cell cultures of osteoblasts with full expression of phenotype, as discussed by Peck, et al., *Endocrinology* 92, 692 (1982). Other studies examining bone cell growth and activity regulation in vitro have identified various factors necessary for cell development, as reported by Beresfor, et al., *Calcif. Tissue Int.* 35, 637 (1983). Studies on osteoblast growth on supports outside of the traditional tissue culture environment have concentrated on studying the growth of these cells on mineral matrices which mimic the natural hydroxyapatite environment in vivo, as reported by Chueng and Haak, *Biomaterials* 10, 63 (1989). Hydroxyapatite (HA), $Ca_3(PO_4)_2.Ca(OH)_2$, is a natural mineral structure that resembles the crystal lattice of bones. Studies on the growth of osteoblasts in culture on calcium phosphate ceramic surfaces demonstrated that osteoblasts, fibroblasts and chondrocytes attach to the ceramic material and form multicellular layers. Retention of phenotypic activity of osteoblasts was demonstrated through parathyroid hormone suppression of alkaline phosphatase activity, and cAMP increase as well as expression of Type I collagen.

The cell source is in some cases determinative of the usefulness of this method. It is clearly most desirable to use a patient's own cells to repair a defect, thereby avoiding problems with immune rejection or contamination. Sources of cells include growing and mature bone, cartilage, and mesenchymal stem cells. Chondro/osteoprogenitor cells, which are bipotent with the ability to differentiate into cartilage or bone, have been isolated from bone marrow (for example, as described by Owen, *J. Cell Sci. Suppl.* 10, 63–76 (1988) and in U.S. Pat. No. 5,226,914 to Caplan, et al.). These cells led Owen to postulate the existence of pluripotent mesenchymal stem cells, which were subsequently isolated from muscle (Pate, et al., *Proc. 49th Ann. Sess. Forum Fundamental Surg. Problems* 587–589 (Oct. 10–15, 1993)), heart (Dalton, et al., *J. Cell Biol.* 119, R202

(March 1993)), and granulation tissue (Lucas, et al., *J. Cell Biochem.* 122, R212 (March 1993)). Pluripotency is demonstrated using a non-specific inducer, dexamethasone (DMSO), which elicits differentiation of the stem cells into chondrocytes (cartilage), osteoblasts (bone), myotubes (muscle), adipocytes (fat), and connective tissue cells. There remains a need for a ready source of cells for use in repairing bone defects.

It is an object of the present invention to provide a method and materials for repair of bone defects, using the patient as the source of cells to thereby avoid immune rejection.

It is a further object of the present invention to provide a method and materials for repair of bone defects, which allows repair of large defects.

It is a further object of the present invention to provide a method and materials for repair of bone defects which ultimately results solely in formation of new bone, without problems relating to long term implantation of foreign materials which could elicit inflammation, bioincompatibility, and poor union with the patient's own bone.

SUMMARY OF THE INVENTION

Methods for repair of bone are disclosed where cells are obtained from periosteum, dissociated, then seeded into an appropriate matrix for repair of the defect. Periosteum consists of multipotent mesodermal cells. The cells are isolated, seeded onto a matrix for implantation, then cultured under conditions which induce the cells to form bone rather than other tissue types, especially cartilage. A variety of different matrix materials can be used to support the dissociated cells. In a preferred embodiment, the material is a biodegradable, biocompatible synthetic polymer such as fibrous polyglycolic acid. Hydrogel matrices can also be used.

Periosteum has been demonstrated to have cell populations that can be isolated in culture, forming both cartilage and bone. In the following example, periosteal cells cultured under osteogenic conditions were used to repair critical size cranial defects in a rabbit model. Periosteum was isolated from New Zealand White (NSW) rabbits, grown in culture, labeled with BrDU, and the cells were seeded into polyglycolic acid (PGA) matrices. Adult NZW rabbits were divided into control and experimental animals and a single 15 mm diameter, full-thickness calvarial defect was made in each rabbit. In the experimental animals, defects were repaired using PGA implants seeded with periosteal cells. In control animals, defects were repaired with untreated PGA implants.

DETAILED DESCRIPTION OF THE INVENTION

Figure 1:
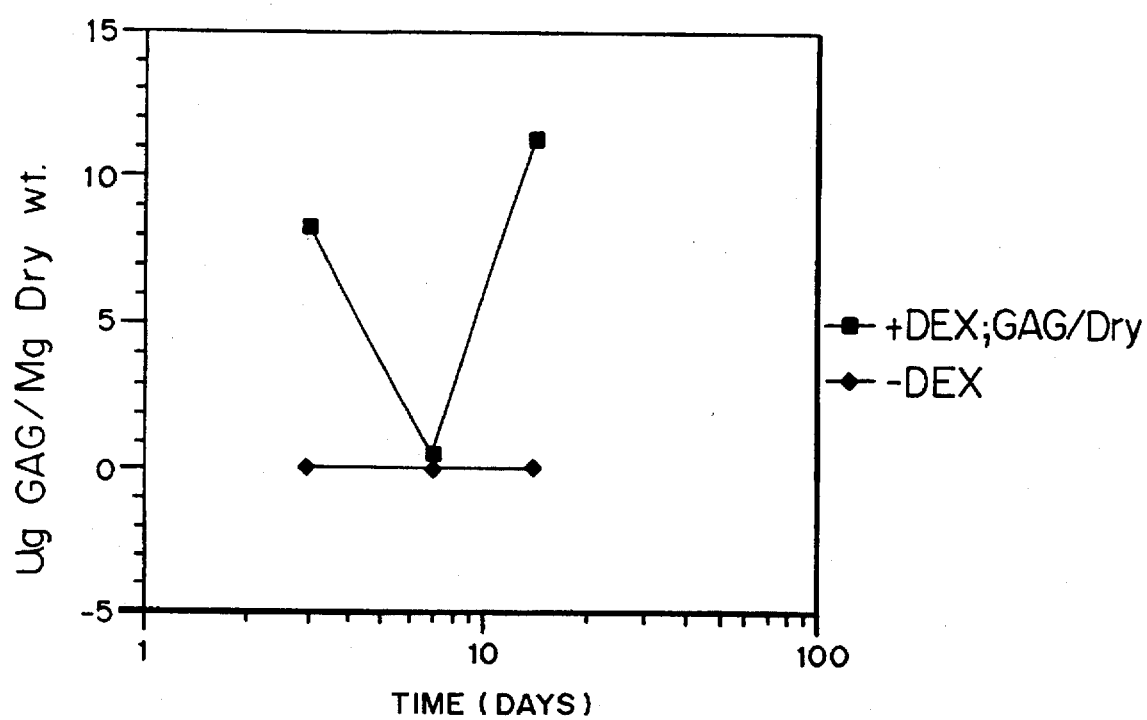
FIG. 1 is a graph of the total glycosaminoglycan (GAG) in periosteal tissue constructs in vitro, micrograms GAG/mg dry weight over time (days), for dexamethasone:GAG/dry (squares) and dexamethasone (diamond).

The disadvantages of autogenous bone grafts, including limited amount of bone and donor site morbidity, have prompted a search for a dependable bone graft substitute. Periosteum has been demonstrated to have cell populations that can be isolated in tissue culture and can form both cartilage and bone. Periosteal cells isolated under chondrogenic conditions and seeded in the polymer scaffolds have been used to repair articular cartilage defects. In the following example, periosteal cells cultured under osteogenic conditions were seeded into resorbable polymer scaffolds and used to repair critical size cranial bone defects.

Periosteum

Periosteum is a dense, white, fibrous covering around the surface of the bone not covered by articular cartilage. The periosteum consists of two layers. The outer fibrous layer is composed of connective tissue containing blood vessels, lymphatic vessels, and nerves that pass into the bone. The inner osteogenic layer contains elastic fibers, blood vessels, and osteoprogenitor cells and osteoblasts. The periosteum is essential for bone growth, repair and nutrition. It also serves as a point of attachment for ligaments and tendons.

Periosteum is obtained by surgically removing the periosteum from bone.

Periosteum consists of multipotent mesodermal cells. Periosteum has the capacity to form all varieties of connective tissue. The proliferative and bone-forming capacity of the osteogenic cells of the periosteal cambium layer has been confirmed in numerous studies. The periosteum culture conditions must be controlled to yield bone. Previous studies have established that transplanted periosteum differentiates based on the type of tissue or bone substrate onto which it is implanted; long bone appears to be better for inducing growth of bone as compared to calvarial bone. It is therefore critical for use of the periosteal cells to form bone to culture the cells under conditions leading to differentiation into bone, rather than cartilage, bone, and other tissues.

Periosteum is obtained by surgical removal of the tissue from the bone. The advantage of the procedure is that it does not require removal of bone per se. The periodsteum is dissected carefully using sharp periosteal elevators. Care is taken to ensure the cambium layer is removed completely. Confirmation of harvest can be accomplished by frozen or conventional histology.

The periosteum is digested using collagenase and trypsin as described by Cohn and Wong, In *Skeletal Research* ed. Simmons and Kunin, p. 3 (Academic Press, NY 1979). Alternatively, cell lines can be established by explant culture. Cells are cultured in Ham's F-12 medium (Gibco) at pH 7.6 supplemented with penicillin (100 U/cc), streptomycin sulfate (100 µg/cc), magnesium sulfate (200 µg/cc), glutamine (58.5 µg/cc) and fetal bovine serum at a final concentration of 12%. Culture medium is replaced three times per week. Cell passage is carried out by incubating monolayers for 5–10 minutes in calcium and magnesium-free Tyrode's solution containing 0.25% trypsin and replating the cells in fresh medium at one-third their confluent density.

Several techniques and materials, alone or in combination, can be employed to promote the osteoblastic phenotype of the periosteal cells, including high oxygen tension, addition of specific compounds or peptides, or specific matrices. In addition to specific matrix interactions, factors determining in vitro differentiation of the cells into bone include high oxygen tension, presence of steroid compounds, especially glucocorticoids such as dexamethasone and other steroidal antiinflammatories and cortisol, proteins and peptides such as calciferol and other enzymes enhancing calcification, beta-glycerolphosphate and other enzymes enhancing phosphorus deposition, prostaglandins such as prostaglandin E2, vitamins C and D and oxygen content. The preferred conditions are described in the following examples. Effective concentrations of the foregoing depend on whether the compounds are used alone or in combination, as well as the relative amounts. Represeitative concentrations include 0.1 µM dexamethasone, 40 ng calciferol/ml culture media, 0.1 µM cortisol, and 0.1 µM prostaglandin E2. Agents which enhance differentiation into cartilage, and which are therefore not advantageous for formation of bone, are known, for example, transforming growth factor beta 1 at concentrations up to 100 ng/ml. In vivo, even if initially induced in vitro to differentiate into bone, the substrate or site of implantation is the primary factor determining differentiation of the cells into bone.

Cells are examined and characterized by both phase contrast microscopy and light reflectance microscopy. Determination of osteoblast-like character is performed through a variety of methods. Osteocalcin production is measured using the method of Gundberg, Lian, and Gallop, *Clin. Chem. Acta* 128, 1 (1983). Monolayer cultures are washed and incubated in serum-free medium containing 10 mg/cc bovine serum albumin in the absence or presence of 10 nM 1,25(dihydroxy)vitaminD$_3$ for 48 hours. The medium is analyzed by radioimmunoassay for osteocalcin at the end of the incubation period.

A number of assays can be used to evaluate the cells. For example, cAMP response to parathyroid hormone (PTH) is measured by incubated cultures near confluency with 1 mM isobutylmethylxanthine alone or in combination with 0.2 to 200 ng/cc of PTH with 1–10 ng/cc calcitonin for 10 minutes at 37° C. Incubations are halted by quickly transferring the cultures to ice, washing rapidly with ice-cold Tyrode's solution, and then adding ice-cold ethanol containing 2 mM HCL. After homogenizing the cells in ethanol for 5 seconds, the samples are dried at 100° C. and cAMP concentrations are measured by radioimmunoassay.

Alkaline phosphatase activity of the cell lysates is determined in a similar manner using the method of Luben, Wong and Cohn, *Endocrinology* 35, 778 (1983) with n-nitrophenylphosphate as substrate. Collagen synthesis is analyzed according to Schwartz. Cultures are incubated for 48 hours in Minimal Essential Medium (Gibco) containing fetal bovine serum (10%), sodium ascorbate (50 microgram/ml), B-aminopropionitrile and tritiated proline (50 UCi/cc). Collagen from the culture medium and cell layer is isolated, treated with pepsin, and after the addition of carrier type I collagen, analyzed by SDS-PAGE under reducing and nonreducing conditions, as described by Neville, *J. Biol. Chem.* 246, 6326 (1971). Banks of carrier protein are identified by staining with Coomassie blue. The gels are then sliced into 25 equal segments each of which is monitored for radioactive content. Collagen distribution is calculated according to the method of Goldberg, et al.,*Biochem. Pharmacol.* 29, 869 (1980).

Matrices for Implantation

The cells are seeded onto and into a matrix for implantation to repair the defect. In the preferred embodiment, the matrix is formed of a synthetic, biocompatible polymer, most preferably a biodegradable polymer, more preferably degrading by hydrolysis rather than enzymolysis. In other embodiments, the matrix is formed of a material such as hydroxyapatite or mixtures of hydroxyapatite and polymer, or tricalcium phosphate. Matrix can also be sterilized bone or a porous metal alloy. The matrix can be in the form of a fibrous or sponge like structure, or a hydrogel. The advantage of the biodegradable material is that the only material ultimately remaining in the patient is the bone. The term "bioerodible", or "biodegradable", as used herein refers to materials which are enzymatically or chemically degraded in vivo into simpler chemical species.

Polymers for Formation of Fibrous Matrices

Over the last decade there has been a tremendous increase in applications for polymeric materials. These materials are well suited to implantation as they can serve as a temporary scaffold to be replaced by host tissue, degrade by hydrolysis to non-toxic products, and be excreted, as described by Kulkarni, et al., *J. Biomedical Materials Research*, 5, 169–81 (1971); Hollinger, J. O. and G. C. Battistone, "Biodegradable Bone Repair Materials, " *Clinical Orthopedics and Related Research*, 207, 290–305 (1986).

Either natural or synthetic polymers can be used to form the matrix, although synthetic polymers are preferred for reproducibility and controlled release kinetics. Synthetic polymers that can be used include bioerodible polymers such as poly(lactide) (PLA), poly(glycolic acid) (PGA), poly(lactide-co-glycolide) (PLGA), and other poly(alphahydroxy acids), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolifins, polyethylene oxide, polyvinyl alcohol, and nylon. Although non-degradable materials can be used to form the matrix or a portion of the matrix, they are not preferred. Examples of natural polymers include proteins such as albumin, collagen, synthetic polyamino acids, and prolamines, and polysaccharides such as alginate, heparin, and other naturally occurring biodegradable polymers of sugar units.

Four polymers widely used in medical applications are poly(paradioxanone) (PDS), poly(lactic acid) (PLA), poly (glycolic acid) (PGA), and PLAGA copolymers. Copolymerization enables modulation of the degradation time of the material. By changing the ratios of crystalline to amorphous polymers during polymerization, properties of the resulting material can be altered to suit the needs of the application. These polymers, including poly(lactide-co-glycolic) acid (PLGA), have been used as polymer composites for bone replacement as reported by H. M. Elgendy, et al. "Osteoblast-like cell (MC3T3-E1) proliferation on bioerodible polymers: An approach towards the development of a bone-bioerodible polymer composite material, " *Biomaterials*, 14, 263–269 (1993). Substituted polyphosphazenes have been shown to support osteogenic cell growth, as reported by C. T. Laurencin, et al. "Use of polyphosphazenes for skeletal tissue regeneration, " *J. Biom. Mater. Res.*, 27 (1993). Poly(organophosphazenes) are high molecular weight polymers containing a backbone of alternating phosphorus and nitrogen atoms. There are a wide variety of polyphosphazenes, each derived from the same precursor polymer, poly(dichlorophosphazene). The chlorine-substituted species can be modified by replacement of the chlorine atoms by different organic nucleophiles such as o-methylphenoxide along with amino acids. The physical and chemical properties of the polymer can be altered by adding various ratios of hydrolytic sensitive side chains such as ethyl glycinate, as described by C. W. R. Wade, et al. "Biocompatibility of eight poly(organophosphazenes), " in *Organomet. Polym.*, C. E. Carraher, J. E. Sheats and C. U. Pitman, Jr., Eds., Academic Press, New York, 1978, pp. 283–288; and H. R. Allcock and T. J. Fuller, "Synthesis and Hydrolysis of Hexakis(imidazolyl)cyclotriphosphazene, " *J. Am. Chem. Soc.*, 103, 2250–2256 (1981). This will affect the degradation of the polymer as an implantable and biodegradable material as well as vary the support of osteogenic cells for bone and tissue implants, as shown by Laruencin, et al. (1993).

PLA, PGA and PLA/PGA copolymers are particularly useful for forming the biodegradable matrices. PLA polymers are usually prepared from the cyclic esters of lactic acids. Both L(+) and D(-) forms of lactic acid can be used to prepare the PLA polymers, as well as the optically inactive DL-lactic acid mixture of D(-) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. Nos. 1,995,970 to Dorough; 2,703,316 to Schneider; 2,758,987 to Salzberg; 2,951,828 to Zeile; 2,676,945 to Higgins; and 2,683,136; 3,531,561 to Trehu. PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", *Chemistry and Industry*, 905 (1970).

The erosion of the matrix is related to the molecular weights of PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives. Poly(lactide-co-glycolide) (50:50), degrades in about six weeks following implantation.

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

These polymers are particularly useful in forming fibrous or sponge type matrices for implantation. Polymers can also be used to form hydrogels in which the cells are suspended and then implanted.

Other Matrix Materials

Another class of materials for making the matrix is hydroxyapatite, or a similar ceramic formed of tricalcium phosphate (TCP) or calcium phosphate ($CaPO_4$).

Calcium hydroxyapatites occur naturally as geological deposits and in normal biological tissues, principally bone, cartilage, enamel, dentin, and cementum of vertebrates and in many sites of pathological calcifications such as blood vessels and skin. Synthetic calcium hydroxyapatite is formed in the laboratory either as pure $Ca_{10}(PO_4)_6(OH)_2$ or hydroxyapatite that is impure, containing other ions such as carbonate, fluoride, chloride for example, or crystals deficient in calcium or crystals in which calcium is partly or completely replaced by other ions such as barium, strontium and lead. Essentially none of the geological and biological apatites are "pure" hydroxyapatite since they contain a variety of other ions and cations and may have different ratios of calcium to phosphorous than the pure synthetic apatites.

In general, the crystals of pure synthetic apatites, geological apatites and many impure synthetically produced apatites are larger and more crystalline than the biological crystals of bone, dentin, cementum and cartilage. The crystals of bone, dentin and cementum are very small, irregularly shaped, very thin plates whose rough average dimensions are approximately 10 to 50 angstroms in thickness, 30 to 150 angstroms in width, and 200 to 600 angstroms in length. The synthetic materials are highly diverse, as reported in the literature. For example, the characterization of four commercial apatites was reported by Pinholt, et al., *J. Oral Maxillofac. Surg.* 50(8), 859–867 (August 1992); *J. Cariofac. Surg.* 1(3), 154–160 (July 1990) reports on a protein, biodegradable material; Pinholt, et al., *Scand. J. Dent. Res.* 99(2), 154–161 (April 1991) reports on the use of a bovine bone material called Bio-Oss™; Friedman, et al., *Arch. Otolaryngol. Head Neck Surg.* 117(4), 386–389 (April 1991) and Costantino, et al., *Arch. Otolaryngol. Head Neck Surg.* 117(4), 379–384 (April 1991) report on a hydroxyapatite cement; Roesgen, *Unfallchirurgle* 16(5), 258–265 (October 1990), reports on the use of calcium phosphate ceramics in combination with autogenie bone; Ono, et al., *Biomaterials* 11(4), 265–271 (May 1990) reports on the use of apatite-wollastonite containing glass ceramic granules, hydroxyapatite granules, and alumina granules; Passuti, et al., *Clin. Orthop.* 248, 169–176 (Nov. 1989) reports on macroporous calcium phosphate ceramic performance; Harada, *Shikwa-Gakuho* 89(2), 263–297 (1989) reports on the use of a mixture of hydroxyapatite particles and tricalcium phosphate powder for bone implantation; Ohgushi, et al., *Acta Orthop. Scand.* 60(3), 334–339 (1989) reports on the use of porous calcium phosphate ceramics alone and in combination with bone marrow cells; Pochon, et al., *Z-Kinderchir.* 41(3), 171–173 (1986) reports on the use of beta-tricalcium phosphate for implantation; and Glowacki, et al., *Clin. Plast. Surg.* 12(2), 233–241 (1985), reports on the use of demineralized bone implants.

As used herein, all of these materials are generally referred to as "hydroxyapatite". In the preferred form, the hydroxyapatite is particles having a diameter between approximately ten and 100 microns in diameter, most preferably about 50 µ in diameter.

Calcium phosphate ceramics can be used as implants in the repair of bone defects because these materials are non-toxic, non-immunogenic, and are composed of calcium and phosphate ions, the main constituents of bone (Jarcho, 1981; Frame, J. W., "Hydroxyapatite as a biomaterial for alveolar ridge augmentation, " *Int. J. Oral Maxillofacial Surgery*, 16, 642–55 (1987); Parsons, et al. "Osteoconductive Composite Grouts for Orthopedic Use, " *Annals N.Y. Academy of Sciences*, 523, 190–207 (1988)). Both tricalcium phosphate (TCP) [$Ca_3(PO_4)_2$] and hydroxyapatite (HA) [$Ca_{10}(PO_4)_6(OH_2)$] have been widely used. Calcium phosphate implants are osteoconductive, and have the apparent ability to become directly bonded to bone. As a result, a strong bone-implant interface is created.

Calcium phosphate ceramics have a degree of bioresorbability which is governed by their chemistry and material structure. High density HA and TCP implants exhibit little resorption, while porous ones are more easily broken down by dissolution in body fluids and resorbed by phagocytosis. However, TCP degrades more quickly than HA structures of the same porosity in vitro. HA is relatively insoluble in aqueous environments. However, the mechanical properties of calcium phosphate ceramics make them ill-suited to serve as a structural element under load bearing circumstances. Ceramics are not preferred since they are brittle and have low resistance to impact loading.

Matrix Configuration

For an organ to be constructed, successfully implanted, and function, the matrices must have sufficient surface area and exposure to nutrients such that cellular growth and differentiation can occur prior to the ingrowth of blood vessels following implantation. The time required for successful implantation and growth of the cells within the matrix is greatly reduced if the area into which the matrix is implanted is prevascularized. After implantation, the configuration must allow for diffusion of nutrients and waste products and for continued blood vessel ingrowth as cell proliferation occurs.

The organization of the tissue may be regulated by the microstructure of the matrix. Specific pore sizes and structures may be utilized to control the pattern and extent of fibrovascular tissue ingrowth from the host, as well as the organization of the implanted cells. The surface geometry and chemistry of the matrix may be regulated to control the adhesion, organization, and function of implanted cells or host cells.

In the preferred embodiment, the matrix is formed of polymers having a fibrous structure which has sufficient interstitial spacing typically in the range of 100 to 300 microns. A microporous structure (pores 205 μm in diameter) has been shown to be too small to permit the ingrowth of cells, as reported by Friedlander, G. E. and V. M. Goldberg, *Bone and Cartilage Allografis, Park Ridge: American Academy of Orthopedic Surgeons,* 1991; Jarcho, M. "Calcium Phosphate Ceramics as Hard Tissue Prosthetics, " *Clinical Orthopedics and Related Research,* 157, 259–78 (1981). As used herein, "fibrous" includes one or more fibers that is entwined with itself, multiple fibers in a woven or non-woven mesh, and sponge like devices.

The overall, or external, matrix configuration is dependent on the tissue which is to be reconstructed or augmented. These are readily determined by the surgeon based on the defect to be corrected.

Polymers for Forming Hydrogels

Polymers that can form ionic hydrogels which are malleable can also be used to support the cells. Injecting a suspension of cells in a polymer solution may be performed to improve the reproducibility of cell seeding throughout a device, to protect the cells from shear forces or pressure induced necrosis, or to aid in defining the spatial location of cell delivery. The injectable polymer may also be utilized to deliver ells and promote the formation of new tissue without the use of any other matrix. In a preferred embodiment, the hydrogel is produced by cross-linking the ionic salt of a polymer with ions, whose strength increases with either increasing concentrations of ions or polymer. The polymer solution is mixed with the cells to be implanted to form a suspension, which is then injected directly into a patient prior to hardening of the suspension. The suspension subsequently hardens over a short period of time due to the presence in vivo of physiological concentrations of ions such as calcium in the case where the polymer is a polysaccharide such as alginate.

A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazenes, and polyacrylates such as hydroxyethyl methacrylate (HEMA), which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolyrically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. Bioerodible polyphosphazenes have at least two differing types of side chains, acidic side groups capable of forming salt bridges with multivalent cations, and side groups that hydrolyze under in vivo conditions, e. g., imidazole groups, amino acid esters, glycerol and glucosyl.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e. g., $R_3N^+$—+$NR_3$ can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005M have been demonstrated to cross-link the polymer. Higher concentrations are limited by the solubility of the salt. The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semipermeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine), examples of synthetic polyamines are: polyethyleneimine, poly(vinylamine), and poly(allyl amine). There are also natural polycations such as the polysaccharide, chitosan. Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

Seeding and Implantation of the Matrix

In the preferred embodiment, the cells are seeded onto and into the matrix, then cultured for a time dependent on the matrix material which is employed. For example, when biodegradable polymeric matrices are used, cells will typically be cultured for between one and five weeks. Cells cultured on matrices formed of a material such as hydroxyapatite can be cultured for between one and ten weeks. The matrix is then surgically implanted at the site of the defect to be corrected, using standard surgical techniques.

In the case of a hydrogel, the polymer is dissolved in an aqueous solution, preferably a 0.1M potassium phosphate solution, at physiological pH, to a concentration forming a polymeric hydrogel, for example, for alginate, of between 0.5 to 2% by weight, preferably 1%, alginate. The isolated cells are suspended in the polymer solution to a concentration of between 1 and 50 million cells/ml, most preferably between 10 and 20 million cells/ml. This is then injected into the site where the repair is needed.

The present invention will be further understood by reference to the following non-limiting examples.

EXAMPLE 1

Repair of Cranial Defects Using Cultured Periosteal Cells

Materials and Methods:

Isolation and Culture of Periosteal Derived *mesenchymal* Stem Cells:

Periosteal tissue was isolated from the proximal tibiae of adult New Zealand White (NZW) rabbits. A 5×10 mm rectangular incision was made to expose the bone, and the periostea was then separated from the underlying bone using sharp periosteal elevators. Care was taken to insure the harvesting of the cambium layer. The tissue was immediately placed in Tyrodes buffer and under sterile conditions diced into small (1 mm) pieces. Explants were placed in Hams F-12 complete tissue culture medium. A second set of explants were cultured in medium supplemented with 0.1 µM dexamethasone. Explants were checked for outgrowth daily and fed fresh medium every other day. Cell lines were serial passaged no more than twice. After cell number amplification was completed, they were trypsinized, washed, and counted. The cells were labeled in log phase of growth in vitro with the nucleic acid analog bromodeoxyuridine (BrDU).

Assembly of Cell Polymer/Tissue Construct Grafts:

The cell pellet was resuspended in 200 µl of medium and then seeded into polyglycolic acid (PGA) non-woven fiber scaffolds (15 mm diam.×2 mm thick, pore size 200 µM) at a density of $4×10^6$ cells/graft. Tissue constructs were allowed to settle for 9 hours in a humidified incubator at 37° C. to allow cells to attach to the scaffold. Assembled tissue constructs were then further cultured for a period of two weeks prior to implantation. In vitro assays of osteoblastic phenotype, including vitamin D stimulation of osteocalcin, and glycosaminoglycan content were performed.

Surgical Procedure:

A total of 24 adult male NZW rabbits were used in this study and divided into control and experimental groups. Rabbits were anesthetized with ketamine/xylazine. Under sterile conditions, a mid-sagittal incision was made and flaps were retracted in a subperiosteal plane, exposing the parietal bone. A 15 mm diameter calvarial defect (critical size defect in the rabbit) was made unilaterally in the parietal bone using a saline cooled trephination drill. In the experimental animals, defects were repaired using a PGA implant seeded with periosteal cells. In the control animals, an untreated PGA implant was used to repair the defects.

Rabbits were divided into groups and euthanized at 4 and 12 weeks after surgery. After sacrifice, the defect site was radiographed and then cut into sagittal halves. One half was fixed in formalin and processed for hematoxylin and eosin (H & E) histology and immunofluorescence studies. The other half was assayed for glycosaminoglycan content, collagen content, and ash weight analysis.

Osteocalcin Assay:

In vitro constructs were incubated with vitamin D ($10^-$2M) for 72 hours. The supernatant was collected, frozen, and the quantity of osteocalcin induced by exposure to vitamin D was determined using a radioimmunoassay.

Total Glycosaminolglycan (GAG) Assay:

The presence of GAG in the repair tissue was determined by the improved DMB method of Farndale. Tissue samples were harvested, dried, weighed, and then digested in a papain-versene solution overnight at 65° C. Aliquots of the tissue digest were then mixed with the dye dimethylene blue (DMB) and read in a spectrophotometer at 535 Å. Chondroitin sulfate was used as a standard for instrument calibration.

Total Collagen Content Assay:

Collagen content in repair sites was assayed using the method of Woessner. Briefly, samples were dried, weighed, and hydrolyzed in 12N HCl at 105° C. for 16 to 24 hours. Samples were mixed with a solution containing Chloramine T heated at 60° C. for 30 minutes and read in a spectrophotometer at 550 nm. Appropriate standards were used for quantitative determination.

Ash Weight Determination:

The amount of bone mineral present at the repair site was determined using a standard ashing method. Replicates of repair tissue from the defect site were harvested, dried at 100° C. for two days, and then weighed. The samples were then placed in an ashing furnace overnight and the sample was then reweighed. Percent bone mineral was then calculated using total dry weight and ash weight.

Histology:

Specimens were fixed in buffered formalin and then decalcified in EDTA, embedded in paraffin, and section were cut at 5 μm in thickness. Slides were stained with H&E and Mallory trichrome.

Cell Labeling and Localization:

Cultured periosteal cells were labeled in log phase of growth in vitro with the nucleic acid analog bromodeoxyuridine (BrDU). Localization was performed using a fluorescein tagged monoclonal antibody and observed under fluorescent microscopy.

Quantitative Radiodensitometry:

Radiographs were taken of the defect site using Kodak x-omat TL film at 50 kV/200 mAs. The area of the defect site on the film was scanned on a Biorad densitometer. Intensity levels were set using normal calvarial bone and blank film.

Figure 2:
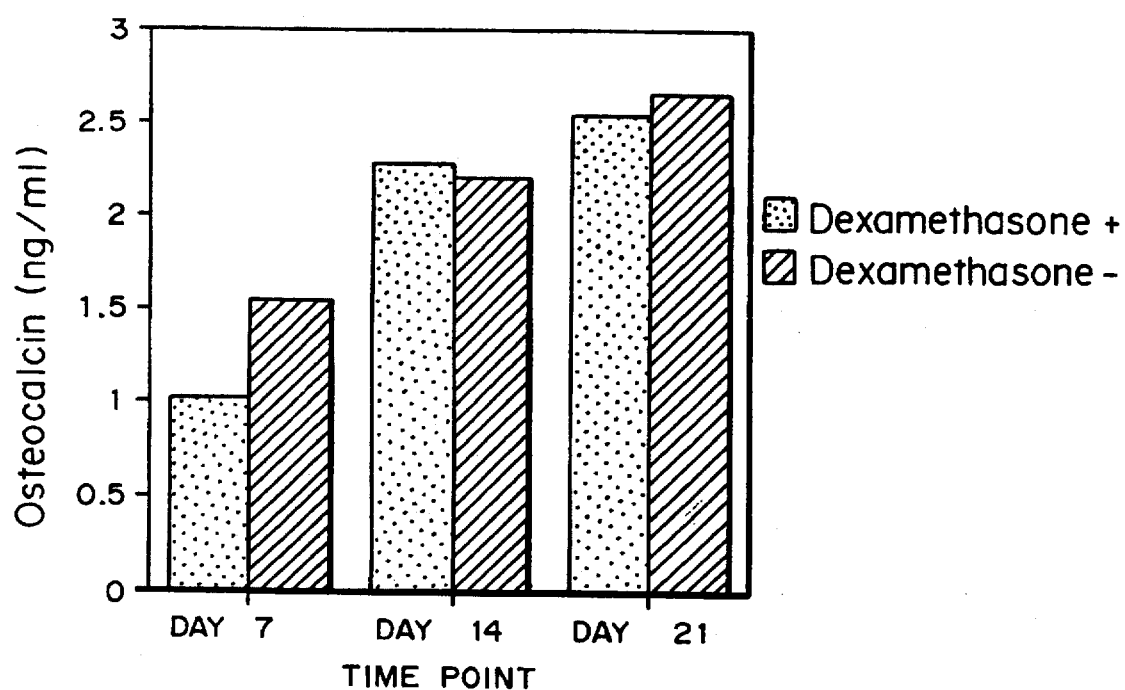
FIG. 2 is a graph of the osteocalcin levels, osteocalcin (ng/ml) at day 7, day 14, and day 21, with dexamethasone (dots) and without dexamethasone (solid).

Results:

In Vitro:

Periosteal cells grew form the explanted tissue within four days after harvest and continued to divide with or without the presence of dexamethasone. However, GAG content was significantly enhanced in constructs cultured with dexamethasone at all time points studied, as shown by FIG. 1. The GAG content did fluctuate with time and did not display any trends. Osteocalcin was produced by the periosteal cells regardless of the presence of dexamethasone. Osteocalcin content increased as a function of time in culture, as shown by FIG. 2. Histological appearance of these calls was fibroblastoid with a spindle morphology in monolayer culture. The morphology was altered when placed into the three dimensional scaffold to a more stellate shape usually with several processes.

Figure 3A:
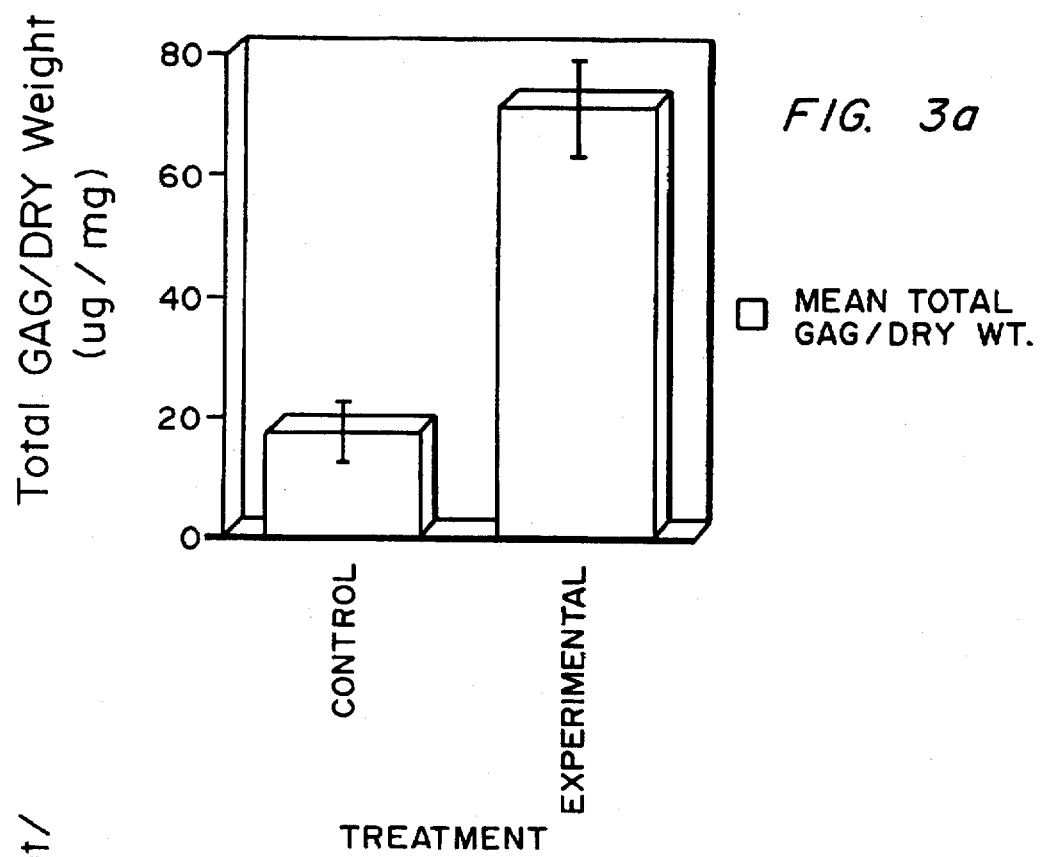
FIGS. 3A, 3B and 3C are graphs of four week in vivo data, glycosaminoglycan content, total GAG/dry weight (micrograms/mg) (FIG. 3A); hydroxyproline content, total hydroxyproline content/dry weight (micrograms/mg) (FIG. 3B); and ash weights, ash weight/dry weight (mg/mg) (FIG. 3C) for control and experimental.
Figure 3B:
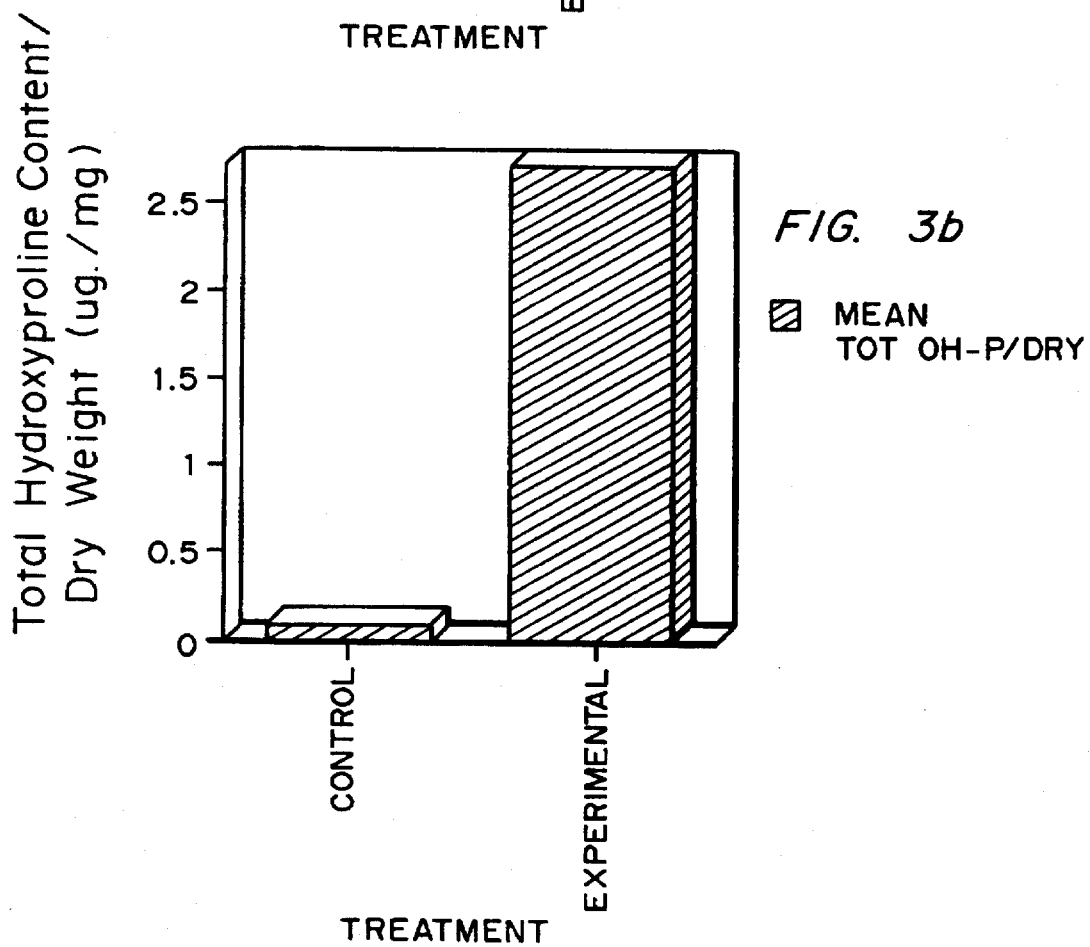
Figure 3C:
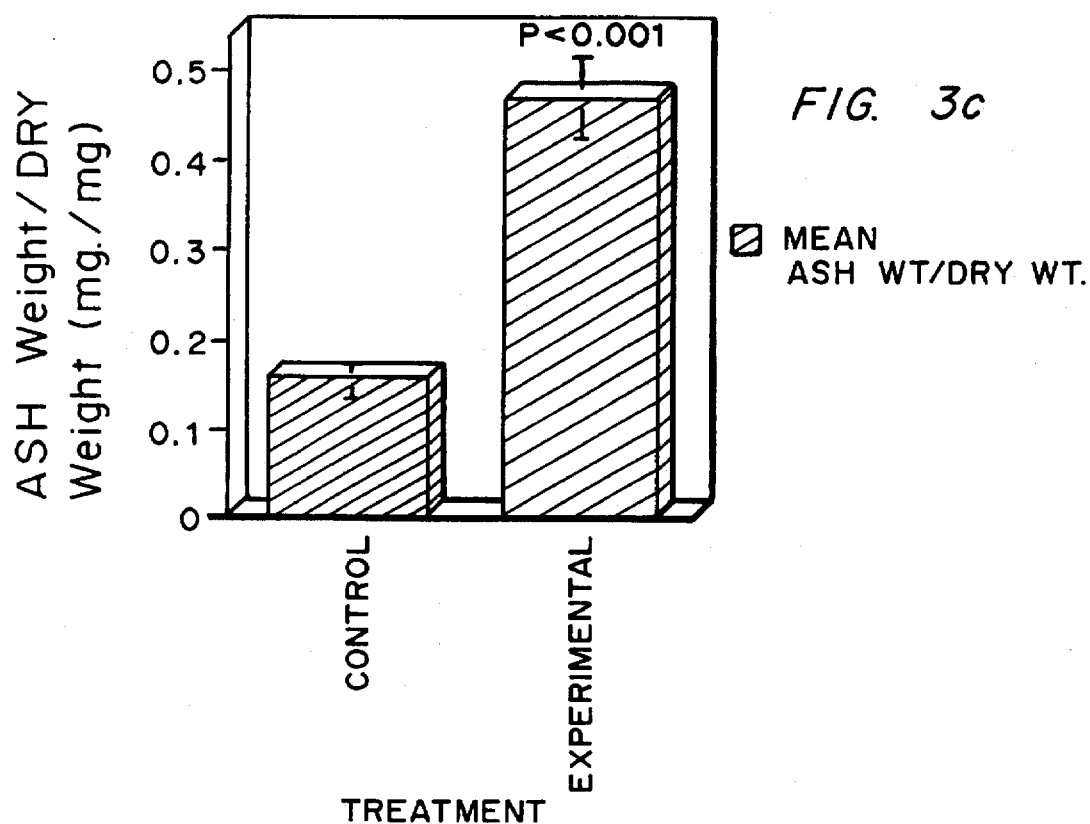

In Vivo:

At four weeks, upon gross examination, the experimental defect sites were filled with a homogenous stiff membrane, whereas the control defect sites were occupied by soft fibrous tissue. H & E histology showed scattered islands of bone in the experimental defects and fibrous tissue in the control defects. Glycosaminoglycan content, collagen content, and ash weight were significantly increased in the experimental defect sites compared with the control defect sites, as shown by FIGS. 3A, 3B and 3C.

Figure 4:
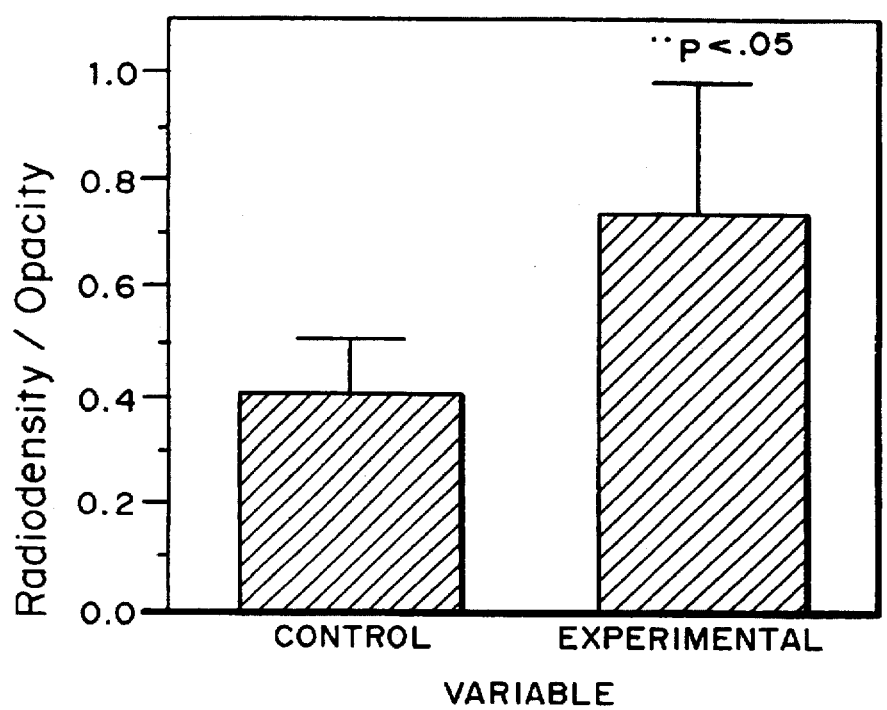
FIG. 4 is a graph of radiodensitometry at twelve weeks post-operative implantation, radiodensity/opacity for control and experimental.

At 8 weeks, although gross and histological examination revealed areas of bone in both the experimental and control defects, there was more bone in the experimental than control defects, there was more bone in the experimental defects. Quantitative analysis of the radiographs (radiodensitometry) showed significantly increased radiopacity in the experimental defects compared with the control defects, as shown by FIG. 4. BrDU fluorescent label was detected in the newly formed bone in the experimental defects confirming the contribution of the cultured periosteal cells to this bone formation.

Summary:

Rabbits were divided into groups and sacrificed at 4 and 12 weeks postoperatively. Repaired defect sites were then studied histologically, biochemically, and radiographically. In vitro analysis of the cultured periosteal cells indicated an osteoblastic phenotype with production of osteocalcin upon stimulation with Vitamin D, as well as increased amounts of glycosaminoglycan. In vivo results at 4 weeks showed islands of bone in the experimental defects, whereas the control defects were filled with fibrous tissue. Glycosaminoglycan content, collagen content, and ash weight were significantly increased in the experimental defects compared with the control defects. At 8 weeks, radiodensitometry demonstrated significantly increased bone formation in the experimental defects compared with the control defects. BrDU fluorescent label was detected in the newly formed bone in the experimental defects, confirming the contribution of the cultured periosteal cells to this bone formation.

Modifications and variations of the present invention will be obvious to those skilled in the art from the foregoing detailed description. Such modifications as to methods for obtaining periosteal cells, culturing the cells, seeding and implanting of a matrix to form new bone or repair bone defects are intended to come within the scope of the appended claims.

We claim:

1. A method for making a composition for repair of bone defects comprising obtaining periosteal tissue, dissociating the cells in the periosteal tissue, and culturing the cells on and in a biocompatible matrix suitable for repair of the defect under conditions inducing the periosteal cells to form bone.

2. The method of claim 1 wherein the matrix is formed of a material selected from the group consisting of hydroxyapatite, synthetic polymers, natural polymers, and mixtures thereof.

3. The method of claim 1 wherein the matrix is biodegradable.

4. The method of claim 1 wherein the matrix is a hydrogel.

5. The method of claim 1 wherein the matrix in combination with an implantation substrate induce the periosteal cells to differentiate into bone.

6. The method of claim 1 wherein the cells are cultured in vitro prior to implantation under conditions inducing differentiation of the periosteal cells into bone.

7. The method of claim 6 wherein the periosteal cells are cultured in on the matrix media comprising inducers of osteogenesis selected from the group consisting of steroids inducing bone formation, enzymes enhancing calcification, enzymes enhancing phosphorus deposition, vitamins, and prostaglandins.

8. The method of claim 7 wherein the inducers are selected from the group consisting of dexamethasone, calciferol, cortisol, vitamin C, vitamin D, and prostaglandin E2.

9. A composition for repair of bone defects comprising cells obtained by dissociating periosteal tissue, wherein the cells are seeded on and in a biocompatible matrix suitable for repair of the defect, and culture conditions inducing the periosteal cells to form bone.

10. The composition of claim 9 wherein the matrix is formed of a material selected from the group consisting of hydroxyapatite, synthetic polymers, natural polymers, and mixtures thereof.

11. The composition of claim 9 wherein the matrix is biodegradable.

12. The composition of claim 10 wherein the matrix is a hydrogel.

13. The composition of claim 9 wherein the matrix induces the periosteal cells to differentiate into bone.

14. The composition of claim 9 wherein the periosteal cells are cultured on the matrix in a culture media comprising inducers of osteogenesis selected from the group consisting of steroids inducing bone formation, enzymes enhancing calcification, enzymes enhancing phosphorus deposition, vitamins, and prostaglandins.

15. The composition of claim 14 wherein the compounds are selected from the group consisting of dexamethasone, calciferol, cortisol, vitamin C, vitamin D, and prostaglandin E2.

* * * * *